United States Patent [19]

Astrove

[11] 4,344,430
[45] Aug. 17, 1982

[54] MEDICATION DIRECTING AID

[76] Inventor: Edgar Astrove, 35 Stratton Rd., Scarsdale, N.Y. 10583

[21] Appl. No.: 246,117

[22] Filed: Mar. 20, 1981

Related U.S. Application Data

[62] Division of Ser. No. 90,330, Nov. 1, 1979, abandoned.

[51] Int. Cl.³ .............................................. A61M 1/00
[52] U.S. Cl. .................................................. 128/233
[58] Field of Search ........................ 128/233, 248, 249

[56] References Cited

U.S. PATENT DOCUMENTS

| | | | |
|---|---|---|---|
| 2,382,771 | 8/1945 | Bowers | 128/233 |
| 2,736,316 | 2/1956 | Stovall | 128/233 |
| 3,506,001 | 4/1970 | Costello | 128/173 |
| 3,779,245 | 12/1973 | Windsor | 128/233 |
| 3,913,575 | 10/1975 | Windsor | 128/233 |

*Primary Examiner*—John D. Yasko
*Attorney, Agent, or Firm*—Carl C. Kling

[57] ABSTRACT

A medication directing aid for use with drop or jelly medication dispensing containers in self-administering medication to medication sites in or near the patient's eye. The medication dispensing container is clamped to the medication directing aid to form a single unit for dispensing the medication and for providing precision direction to the dispenser tip. The medication directing aid comprises a mirror surface and a clamp, integral to a carrier and juxtaposed at an angle of approximately 135 degrees. When assembled the medication directing aid and the medication dispensing container together form a medication dispensing-viewing unit which may be positioned and operated with one hand and one eye.

9 Claims, 6 Drawing Figures

MEDICATION DIRECTING AID

This is a division of United States patent application Ser. No. 90,330, filed Nov. 1, 1979, now abandoned entitled MEDICATION DIRECTING AID.

BRIEF SUMMARY OF THE INVENTION

The invention is a dropper medication directing aid for putting medication on a desired medication site in the vicinity of the eye. The patient makes a simple assembly of the medication directing aid and the dispensing container and with one hand holding the assembly administers medication with precision, with minimum waste and spill. In operation, the patient views the image of both the tip of the dispensing container and the medication site on the mirror surface of the medication directing aid. The medication directing aid is conveniently positioned and supported as a single unit with the medication dispensing container.

Self-administering medication into the eye, or even near the eye, is a difficult task, particularly if the patient has visual or other impairment. Known medication directing aids include such inappropriate devices as the bathroom mirror, eyecup sprays and even eyeglasses with a hole drilled to position a dropper.

The object of the invention is to ameliorate the difficulty associated with proper self-administering of medication in the vicinity of the eye.

The medication directing aid comprises a mirror surface and a clamp, integral to a carrier and juxtaposed at an angle of approximately 135 degrees.

An advantage of the invention is its capability of being formed with optical correction capability.

Another advantage of the invention is that it is readily portable, either clamped to a medication dispensing container or detached, and readily stored with the medication.

An advantage of the invention is that it requires only one hand, either right or left, and only one eye, either right or left, to operate. Obviously it also may be operated with both hands and with both eyes by patients without visual or manual handicap.

Another advantage is that the invention is easily manufactured of inexpensive, durable materials, and may be packaged along with its associated medication dispensing container in a box having its longest dimension considerably shorter than the longest dimension of the medication directing aid.

DRAWINGS

DESCRIPTION OF THE PREFERRED EMBODIMENT

Figure 1:
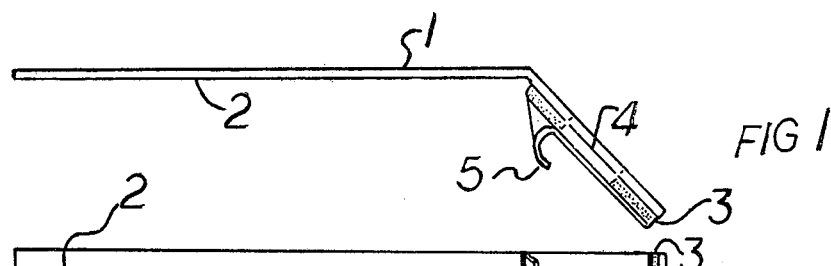
FIG. 1 is an elevation view of a preferred embodiment.
Figure 2:
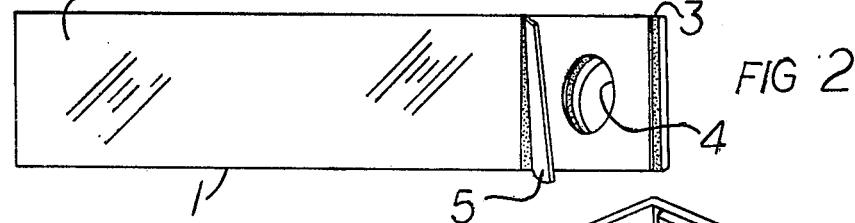
FIG. 2 is a plan view of the preferred embodiment of FIG. 1.

The medication directing aid comprises in the preferred embodiment three operational elements, one of which elements is dual-purpose. The elements are carrier 1, mirror viewing surface 2, and dual-purpose clamp 3,4. In addition, there is a packaging element, protective peelstrip 5.

Carrier 1 is preferably aluminum metallized polyester of suitable thickness to be self supporting, approximately 7 mils. Such materials are commercially available. Carrier 1 is formed with a sharp corner bend formed so as to exceed the elastic limit of the material so as to retain a "memory" even if folded or flattened for convenient shipping or storage. The mirror viewing surface 2 in the preferred embodiment is approximately 25 by 75 millimeters, although there is nothing critical about the dimensions and the patient may easily trim the mirror to his own liking with scissors. A glass mirror might be substituted for the metallized polyester, possibly even with optical advantages, but the metallized polyester is the material of choice because it is easily cleaned when soiled, unbreakable and shatterproof, easily modified in shape by the patient, capable of being looped for storage in a cramped medication container packaging box, lightweight and of such low mass that it is relatively fog-free when taken from refrigerated storage for immediate use. The portion of the carrier on the arm of carrier 1 opposite mirror viewing surface 2 need not be metallized, although for manufacturing economy it is cheaper to use fully metallized stock rather than to take special steps to metallize only the mirror viewing surface.

Carrier 1 is preferably formed with an obtuse angle of approximately 135 degrees about its fold, forming a mirror arm and a relatively short clamping arm. While special metal or plastic clamps could be devised, or the patient could provide a clamp with his fingers, a simple locating clamp made up of pad 3 of double-sided adhesive of any commercial variety, preferably restickable, is satisfactory. Pad 3 should be of substantial thickness, preferably of the foam type, so as to accommodate a variety of medication dispensing containers of various shapes.

Pad 3 is preferably formed with an aperture 4 which also extends through the clamping arm of carrier 1. This aperture, while not required for medication dispensing containers of the squeeze bottle or tube type, is helpful in properly locating the medication dispensing container. Aperture 4 is primarily for serving as a clamp to dispensers of the squeeze bulb type.

Figure 3:
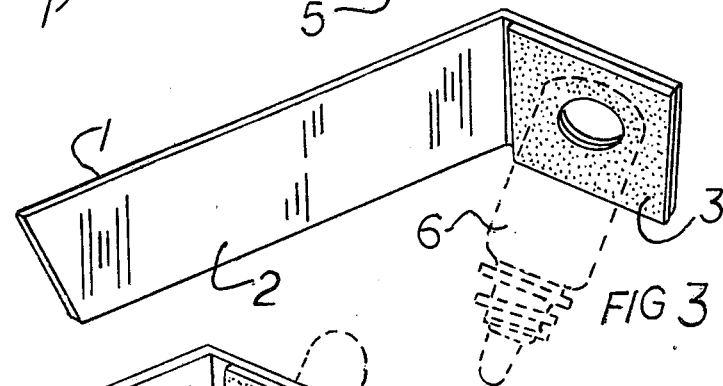
FIG. 3 is a perspective view of the preferred embodiment of FIGS. 1 and 2 ready for use clamped to a plastic medication dispenser bottle.

FIG. 3 shows the preferred embodiment of the invention in use with a medication dispensing container of the squeeze bottle type. Squeeze bottle 6 is shown in phantom, mounted adhesively to the clamping arm of carrier 1.

Figure 4:
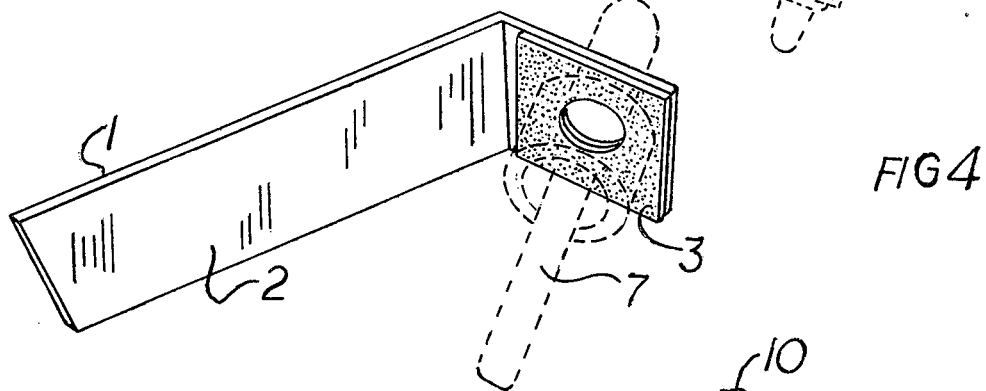
FIG. 4 is a perspective view of the preferred embodiment of FIGS. 1 and 2 clamped to a squeeze bulb dropper medication dispensing container.

FIG. 4 shows the preferred embodiment of the invention in use with a medication dispensing container of the squeeze bulb type. Squeeze bulb dropper 7, with its integral bottle cap, is shown in phantom. Adhesive pad 3 helps to hold the dropper in place by gripping the cap, but frictional clamping of a capless dropper bulb (not shown) is also available. Other types of medication delivery devices such as swabs or jelly tubes can with care be clamped similarly through the aperture.

Figure 5:
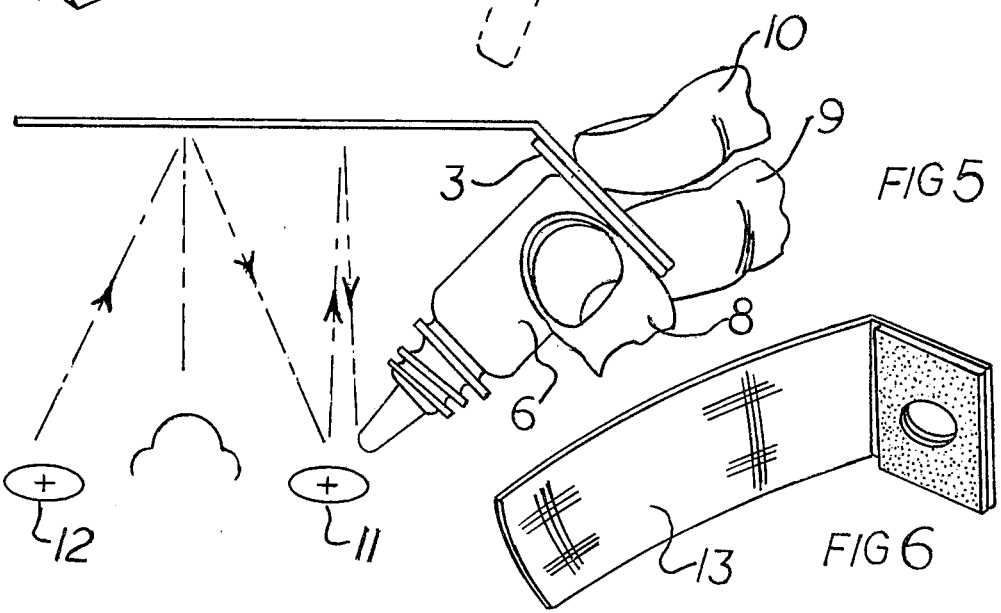
FIG. 5 is an operational schematic diagram.

FIG. 5 shows schematically how the medication directing aid is used. The patient has adhesively attached medication dispensing container 6 to pad 3 to form a single unit of the medication directing aid and the medication dispensing container, and is holding the unit in fingers 8, 9, 10 of his right hand, in proper dispensing and viewing attitude above his right eye 11. The patient views the image of both his right eye 11 and his left eye 12, as indicated by the sight lines. If vision in either eye is impaired, he can view with the good eye alone. If use of either hand is impaired, he can operate the combined medication directing aid and medication dispensing container with the good hand. If both eyes have good vision, he can view with both. If both hands are free and operative, he can operate the combined medication directing aid and medication dispensing container with one hand and use the other hand to roll down the eyelid or hold a tissue in place to absorb the spill, or manipulate the curvature of the mirror, or a combination of these. When self-dispensing of medication is completed, the medication directing aid may conveniently be left attached to the medication dispensing container for storage. The medication directing aid may be stored still attached to a cap type squeeze bulb dropper after the dropper has been replaced in the bottle. The medication directing aid may be stored with a dropper bottle by simply standing the bottle on top of the medication directing aid on a shelf.

Figure 6:
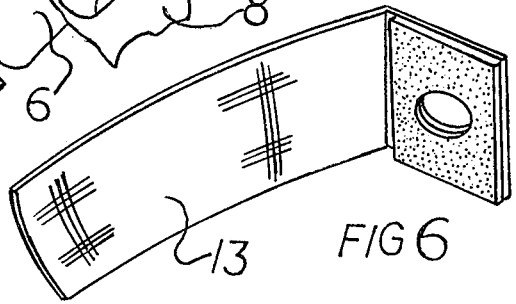
FIG. 6 is a three-dimensional perspective view of a second embodiment having built-in optical correction.

FIG. 6 illustrates a variation having optical correction built in. During manufacture, a very slight curvature along its longitudinal axis is built into the material forming the mirror arm 13 of the carrier. This slight curvature (shown exaggerated) provides magnification, which adds convenience for patients who desire the magnification. In addition, a slight curvature may be formed into mirror arm 13 of the carrier in the direction normal to the longitudinal axis, forming a compound concave mirror which, because it remains essentially flat at the fold, has a wide range of differential optical corrections along its length.

The slight curvature also adds beam strength to the medication directing aid which prevents wobble. Even without optical correction, a slight bend or embossment at the edges of the carrier adds beam strength. The patient can provide a sturdy base for the medication directing aid by resting his fingers on his nose or brow and resting the medication directing aid on a finger.

CONCLUDING SUMMARY

The medication directing aid yields an inexpensive, convenient and effective viewing aid for permitting accurately directed self-medication at sites in the vicinity of the eye. After use, the medication directing aid may conveniently be left clamped to the medication dispensing container for storage as a unit in refrigerator or cabinet. Patients having a visual impairment of the type commonly described as "far-sighted" may need to extend the focal length of the medication directing aid by adding a spacer to pad 3 or even to forming a sort of accordian pleat in carrier 1 at the fold. Patients with the problem of quaking hands may find it advantageous to steady the extended end of the mirror arm of carrier 1 with a finger of the "free" hand, which at the same time may also be rolling the eyelid, etc. Patients who require magnification may achieve the desired effect by forming or holding the mirror arm 2 of carrier 1 in a curvature appropriate to the need for magnification, which can be quickly learned. Magnification may also be provided by manufacturing the mirror with simple or compound curvatures.

What is claimed is:

1. A medication directing aid characterized by:
   (a) a carrier having a mirror arm and a medication dispenser clamping arm formed of self-supporting flexible material at an obtuse angle;
   (b) a mirror viewing surface on the mirror arm of said carrier (a); and
   (c) clamping means associated operatively with the medication dispenser clamping arm of said carrier, to clamp a medication dispenser in place, comprising adhesive material disposed about a locating point on said clamping arm so as to present an adhesive clamping face on said carrier (a).

2. A medication directing aid characterized by:
   (a) a carrier having a mirror arm and a medication dispenser clamping arm formed of self-supporting material at an obtuse angle;
   (b) a mirror viewing surface on the mirror arm of said carrier (a);
   (c) clamping means associated operatively with the medication dispenser clamping arm of said carrier
   (d) an aperture in the medication dispenser clamping arm of said carrier (a); and
   (e) adhesive material mounted about said aperture (d) on said carrier (a) so as to present an adhesive clamping face about said aperture facing outward from said carrier (a).

3. A medication directing aid according to claim 1, further characterized in that said carrier (a) is formed of self-supporting metallized mirror plastic sheet formed to an angle of approximately 135 degrees, and further characterized in that there is an aperture in the medication dispenser clamping arm of said carrier (a); and said clamping means (c) comprises an apertured pad of two-sided adhesive mounted on the medication dispenser clamping arm of said carrier (a) so as to present an adhesive clamping face about the aperture in said carrier (a) facing outward from said carrier (a).

4. A medication directing aid according to claim 3, further characterized by:
   a peelstrip removably mounted atop the outward face of the two-sided adhesive of said clamping means (c).

5. A medication directing aid according to claim 1, further characterized by:
   means to form a range of optical correction configurations of said carrier and mirror.

6. A medication directing aid according to claim 5, in which said optical correction is an altered focal length.

7. A medication directing aid according to claim 5, in which said optical correction is magnification.

8. A medication directing aid according to claim 1, further characterized by a configuration adding beam stiffness along the mirror arm of said carrier.

9. A medication directing aid according to claim 8, in which the configuration adding beam stiffness along the mirror arm of said carrier is a slight curvature.

* * * * *